United States Patent
Shimizu et al.

(10) Patent No.: US 9,855,407 B2
(45) Date of Patent: Jan. 2, 2018

(54) GUIDE WIRE

(71) Applicant: ASAHI INTECC CO., LTD., Nagoya-shi, Aichi (JP)

(72) Inventors: Eriko Shimizu, Seto (JP); Shinichi Ashida, Izumi (JP)

(73) Assignee: ASAHI INTECC CO., LTD., Nagoya (JP)

( * ) Notice: Subject to any disclaimer, the term of this patent is extended or adjusted under 35 U.S.C. 154(b) by 35 days.

(21) Appl. No.: 14/818,657

(22) Filed: Aug. 5, 2015

(65) Prior Publication Data

US 2016/0089514 A1 Mar. 31, 2016

(30) Foreign Application Priority Data

Sep. 26, 2014 (JP) ................. 2014-196231

(51) Int. Cl.
*A61M 25/09* (2006.01)
(52) U.S. Cl.
CPC ... *A61M 25/09* (2013.01); *A61M 2025/09083* (2013.01); *A61M 2025/09108* (2013.01); *A61M 2025/09175* (2013.01); *A61M 2025/09191* (2013.01)
(58) Field of Classification Search
CPC ......... A61M 2025/09191; A61M 2025/09083; A61M 2025/09108; A61M 2025/09175; A61M 25/09
See application file for complete search history.

(56) References Cited

U.S. PATENT DOCUMENTS

| 2005/0054950 A1 | 3/2005 | Parins |
| 2005/0154371 A1 | 7/2005 | Miyata et al. |
| 2007/0185415 A1 | 8/2007 | Ressemann et al. |
| 2010/0023035 A1 | 1/2010 | Kontos |
| 2011/0009806 A1* | 1/2011 | Melsheimer .......... A61M 25/09 604/21 |
| 2011/0319872 A1 | 12/2011 | Kawasaki |
| 2012/0041420 A1* | 2/2012 | Nagano ................. A61M 25/09 604/528 |

FOREIGN PATENT DOCUMENTS

| EP | 2 415 497 A1 | 2/2012 |
| EP | 2 586 483 A1 | 5/2013 |
| JP | 2008-155052 A | 7/2008 |
| JP | 4354523 B1 | 10/2009 |
| JP | 2012-192177 A | 10/2012 |

OTHER PUBLICATIONS

Mar. 11, 2016 Extended European Search Report issued in European Patent Application No. 15185388.4.

* cited by examiner

Primary Examiner — Rene Towa
(74) Attorney, Agent, or Firm — Oliff PLC

(57) ABSTRACT

A guide wire includes (1) a core shaft, (2) a coil body covering a distal end portion of the core shaft and having spirally wound multiple element wires, and (3) a distal end fixed portion by which a distal end of the core shaft is fixed to a distal end of the coil body. The distal end of the coil body includes (i) a fixed portion in which adjacent ones of the multiple element wires are fixed to each other and (ii) a gap portion in which adjacent ones of the multiple element wires are not fixed to each other to provide a gap between the adjacent ones of the multiple element wires in the gap portion, as viewed in a cross section that is perpendicular to a longitudinal axis of the guide wire. The distal end fixed portion enters into the gap portion.

5 Claims, 11 Drawing Sheets

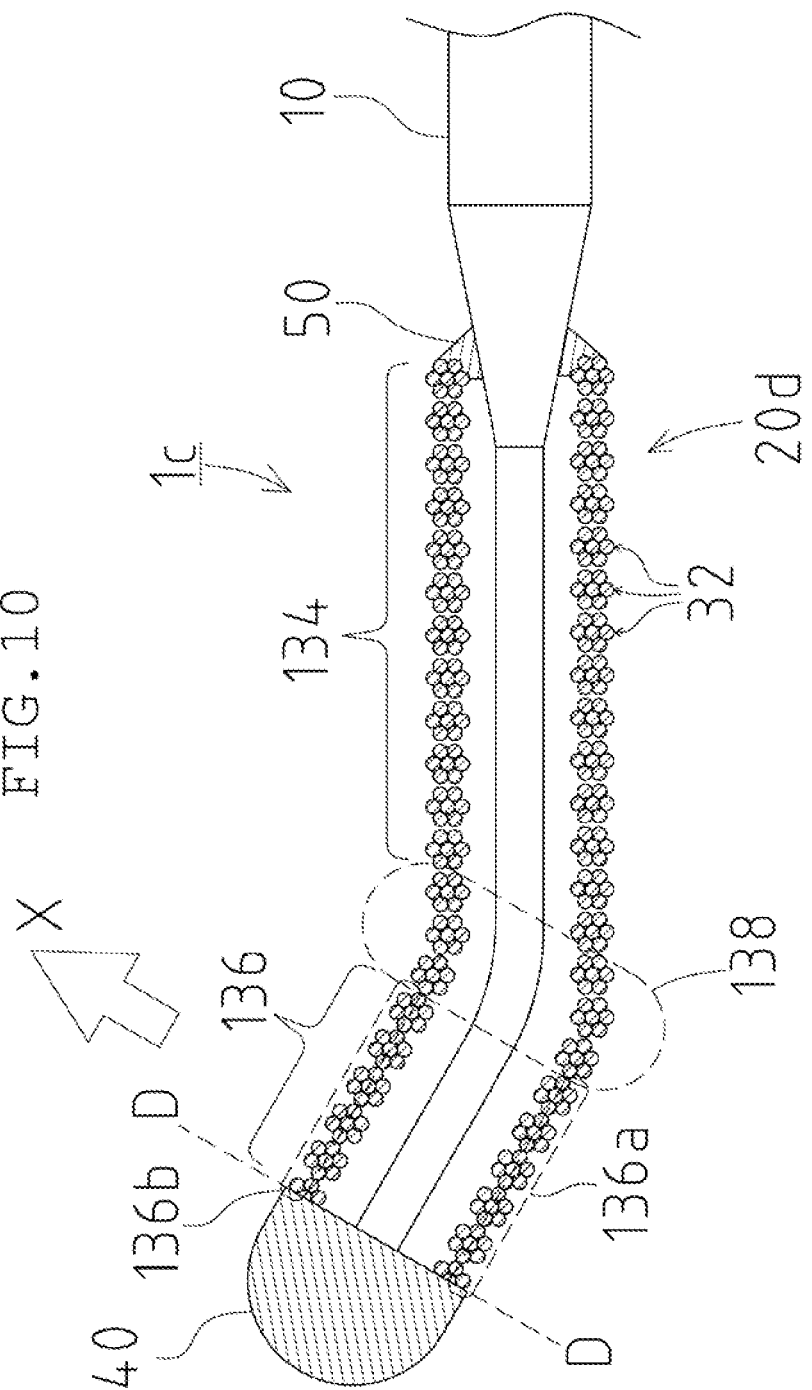

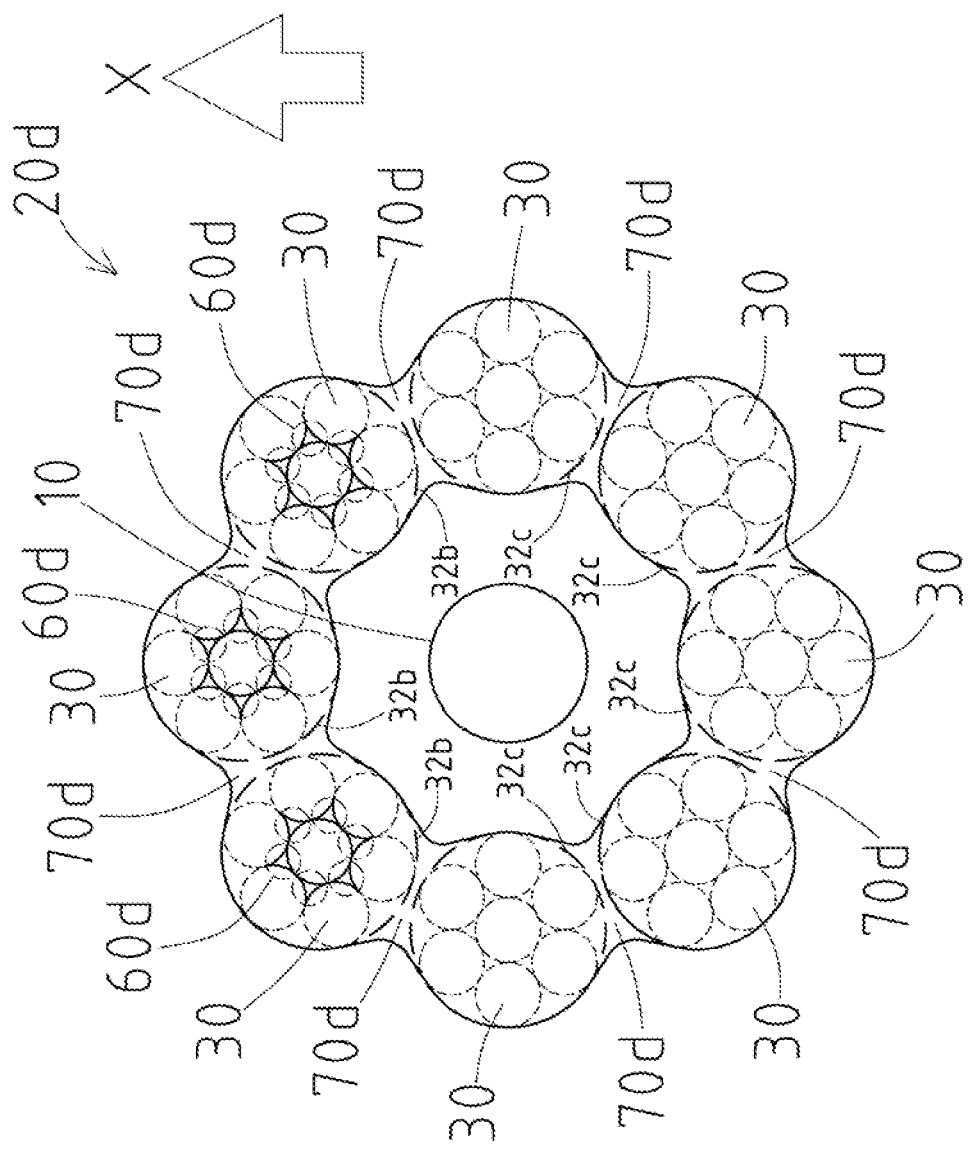

GUIDE WIRE

CROSS REFERENCE TO RELATED APPLICATION

This application claims priority to Japanese Application No. 2014-196231 filed on Sep. 26, 2014, the content of which is incorporated by reference herein in its entirety.

The disclosed embodiments relate to a guide wire to be inserted into a blood vessel or digestive organ for the purpose of treatment or examination.

BACKGROUND

When a narrowed or obstructed part is formed in a blood vessel, bile duct, pancreatic duct and the like, the flow of blood, bile (gall), pancreatic fluid and the like may be hindered. Conventionally, a treatment for improving the flow of blood, bile (gall), pancreatic fluid and the like is widely performed by inserting a guide wire into a narrowed or obstructed part, and then expanding the narrowed or obstructed part with a balloon catheter which follows the guide wire.

Various guide wires intended for guiding a balloon catheter to a narrowed or obstructed part have been proposed. For example, Japanese Patent No. 4354523 discloses a guide wire comprising a core shaft, a coil body covering a distal end portion of the core shaft and formed with one wound element wire and a distal end fixed portion where the distal end of the core shaft is fixed to the distal end of the coil body. Japanese Patent Application Laid-Open No. 2008-155052 discloses a guide wire comprising a core shaft, a coil body covering a distal end portion of the core shaft and formed with spirally wound multiple element wires and a distal end fixed portion where the distal end of the core shaft is fixed to the distal end of the coil body.

However, in such guide wires, multiple element wires of a coil body are not welded to each other at the distal end of the coil body. Therefore, when fixing the distal end of a core shaft to the distal end of a coil body at a distal end fixed portion, the following problems occur: (i) the distal end fixed portion may flow towards the proximal end side along the surfaces of all of the multiple element wires, and thus the length of the distal end fixed portion is difficult to control; and (ii) the multiple element wires of the coil body may become unwound, and thus the distal end fixed portion is difficult to be fixed to the distal end of the coil body.

Further, although it is not a guide wire, a catheter is known in which an end of a coil body formed with spirally wound multiple element wires is connected to an end of a braid by welding. In that known catheter, the braid comprises a first element wire and a second element wire braided in a net-like structure (see Japanese Patent Application Laid-Open No. 2012-192177). In the catheter described in Japanese Patent Application Laid-Open No. 2012-192177, multiple element wires of the coil body are melted together to fix the element wires to each other in order to improve the connectivity between the coil body and the braid.

When the coil body disclosed in Japanese Patent Application Laid-Open No. 2012-192177 is applied to the guide wires of the Japanese patent and published application described above, the flow of the distal end fixed portion towards the proximal end side along the multiple element wires might be prevented, and further the distal end fixed portion might be easily fixed to the distal end of the coil body. However, the tensile strength of the distal end fixed portion becomes weak, resulting in a risk that the distal end fixed portion becomes detached from the distal end of the coil body since the distal end fixed portion is only fixed to an end face of the distal end of the coil body (in other words, the distal end fixed portion does not flow towards the proximal end side along the multiple element wires at all).

SUMMARY

The disclosed embodiments have been made in view of the circumstances described above. An object of embodiments is to provide a guide wire in which both a fixed portion and a gap portion are provided at the distal end of a coil body, and a distal end fixed portion can be easily fixed to the distal end of the coil body by allowing the distal end fixed portion to enter into the gap portion, and the distal end fixed portion does not easily become detached from the distal end of the coil body.

A first aspect of the disclosed embodiments relates to a guide wire comprising a core shaft, a coil body covering a distal end portion of the core shaft and having spirally wound multiple element wires, and a distal end fixed portion by which a distal end of the core shaft is fixed to a distal end of the coil body. The distal end of the coil body comprises (i) a fixed portion in which adjacent ones of the multiple element wires are fixed to each other and (ii) a gap portion in which adjacent ones of the multiple element wires are not fixed to each other to provide a gap between the adjacent ones of the multiple element wires in the gap portion as viewed in a cross section perpendicular to a longitudinal axis of the guide wire. The distal end fixed portion enters into the gap portion.

A second aspect of the disclosed embodiments relates to the guide wire according to the first aspect, wherein each of the element wires is a twisted wire such that the coil body has spirally wound multiple twisted wires, and adjacent ones of the multiple twisted wires are fixed to each other by the fixed portion at the distal end of the coil body as viewed in the cross section perpendicular to the longitudinal axis of the guide wire, and the gap portion is formed inside of at least one twisted wire of the multiple twisted wires.

A third aspect of the disclosed embodiments relates to the guide wire according to either of the first or second aspects described above, wherein the distal end portion of the coil body is curved in a curvature direction so as to have an inner periphery side and an opposite, outer periphery side relative to the curvature direction, the fixed portion is located on the outer periphery side of the coil body, and the gap portion is located on the inner periphery side of the coil body.

In the guide wire according to the first aspect, a fixed portion in which adjacent ones of the multiple element wires are fixed to each other and a gap portion in which adjacent ones of the multiple element wires are not fixed to each other to leave a gap between the adjacent ones of the multiple element wires in the gap portion as viewed in the cross section perpendicular to the guide wire longitudinal axis are provided at the distal end of the coil body, and a distal end fixed portion enters into the gap portion. Because both the fixed portion and the gap portion are provided at the distal end of the coil body, a risk of unwinding of the multiple element wires of the coil body can be reduced. Further, a risk can be reduced that the distal end fixed portion flows towards the proximal end side along the surfaces of all of the multiple element wires even in a case where highly flowable (highly wettable) solder materials and metal solders are used at the distal end fixed portion. Moreover, the tensile strength of the distal end fixed portion can be enhanced because the distal end fixed portion enters into the gap portion. Therefore, a risk that the distal end fixed portion becomes detached from the distal end of the coil body can be reduced even when external force is applied to the distal end of the coil body.

In the guide wire according to the second aspect, the coil body is formed with spirally wound multiple twisted wires in which multiple element wires are twisted, adjacent ones of the multiple twisted wires are fixed to each other by the fixed portion, and the gap portion is formed inside of at least one twisted wire of the multiple twisted wires. The coil body has a degree of freedom and high flexibility because the coil body is formed with multiple twisted wires. On the other hand, multiple twisted wires of a coil body tend to unwind more easily as compared with a coil body formed with a spirally wound single wire or spirally wound multiple element wires. However, in the guide wire according to the second aspect, the distal end of the coil body does not easily unwind even in a case where the coil body is formed with multiple twisted wires because adjacent ones of the twisted wires are fixed to each other by the fixed portion. Further, because the distal end fixed portion enters into the gap portion formed inside of a twisted wire, a risk that the distal end fixed portion peels off from the coil body can be reduced even in a case where the distal end of the coil body is strongly rubbed with a narrowed or obstructed segment when an operator pushes the guide wire into the narrowed or obstructed segment. As a result, a risk that the distal end fixed portion becomes detached from the distal end of the coil body can be further reduced.

In the guide wire according to the third aspect, the distal end portion of the coil body is curved in a curvature direction so as to have an inner periphery side and an opposite, outer periphery side relative to the curvature direction, the fixed portion is located on the outer periphery side of the coil body while the gap portion is located on the inner periphery side of the coil body. Therefore, the distal end fixed portion is configured to easily enter into the gap portion formed in the same direction as the curvature direction of the coil body (the inner periphery side), but not into the fixed portion formed in the opposite direction of the curvature direction of the coil body (the outer periphery side). By this structure, the distal end fixed portion does not flow towards the proximal end side in the opposite direction of the curvature direction of the coil body (in other words, the outer periphery side of the coil body) which tends to make contract with a blood vessel wall and a digestive organ wall when a guide wire is inserted into a blood vessel or digestive organs. On the other hand, the distal end fixed portion flows towards the proximal end side in the same direction as the curvature direction of the coil body (in other words, the inner periphery side of the coil body) which tends not to make contact with a blood vessel wall or digestive organ wall. As a result, because the distal end fixed portion preferentially enters into the inner periphery side over the outer periphery side, a risk of damaging a wall of a blood vessel or a digestive organ wall with the outer periphery side of the coil body can be reduced when a guide wire is inserted into a blood vessel or a digestive organ.

BRIEF DESCRIPTION OF THE DRAWINGS

FIG. 10 shows an overall view of a guide wire according to embodiments of the present invention.
FIG. 11 shows the D-D cross section in FIG. 10.

DETAILED DESCRIPTION OF EMBODIMENTS

First, a guide wire 1 according to embodiments will be described with reference to FIGS. 1 to 3. The left side in FIGS. 1 and 3 corresponds to the distal end (the front end) which is to be inserted into the body, and the right side corresponds to the proximal end (the base end) which is to be operated by an operator such as a physician. FIG. 2 shows the A-A cross section in FIG. 1, which is a cross section perpendicular to the longitudinal axis of the guide wire.

Figure 1:
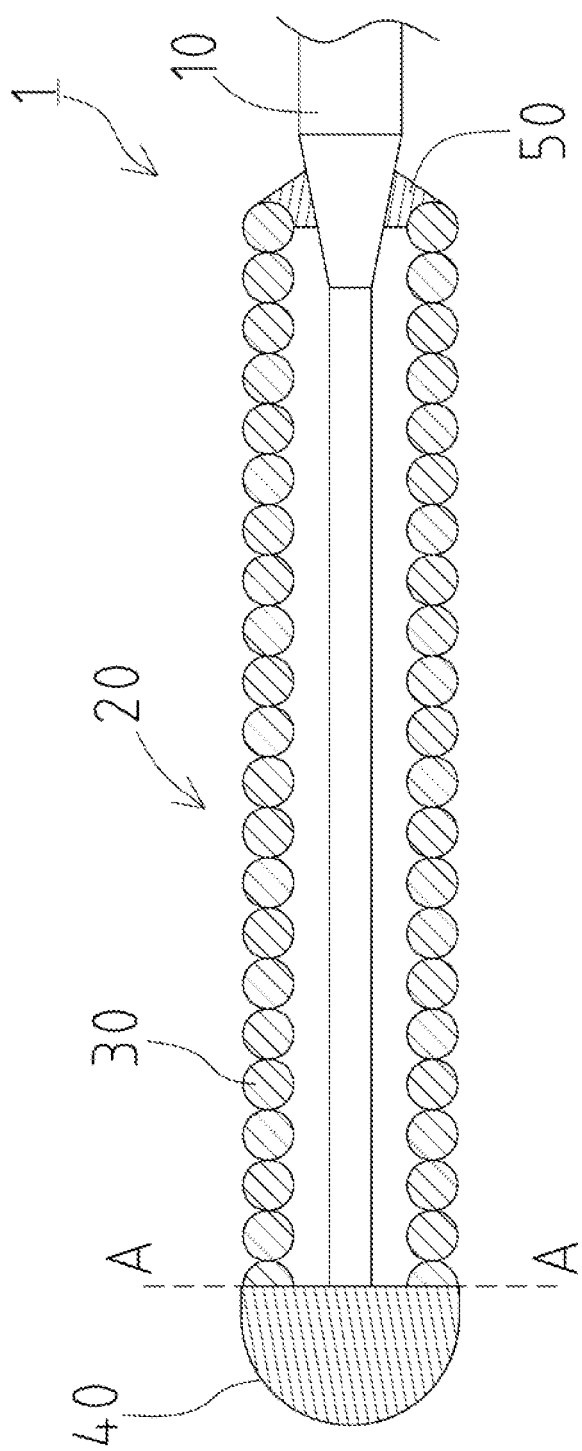
FIG. 1 shows an overall view of a guide wire according to embodiments of the present invention.
Figure 2:
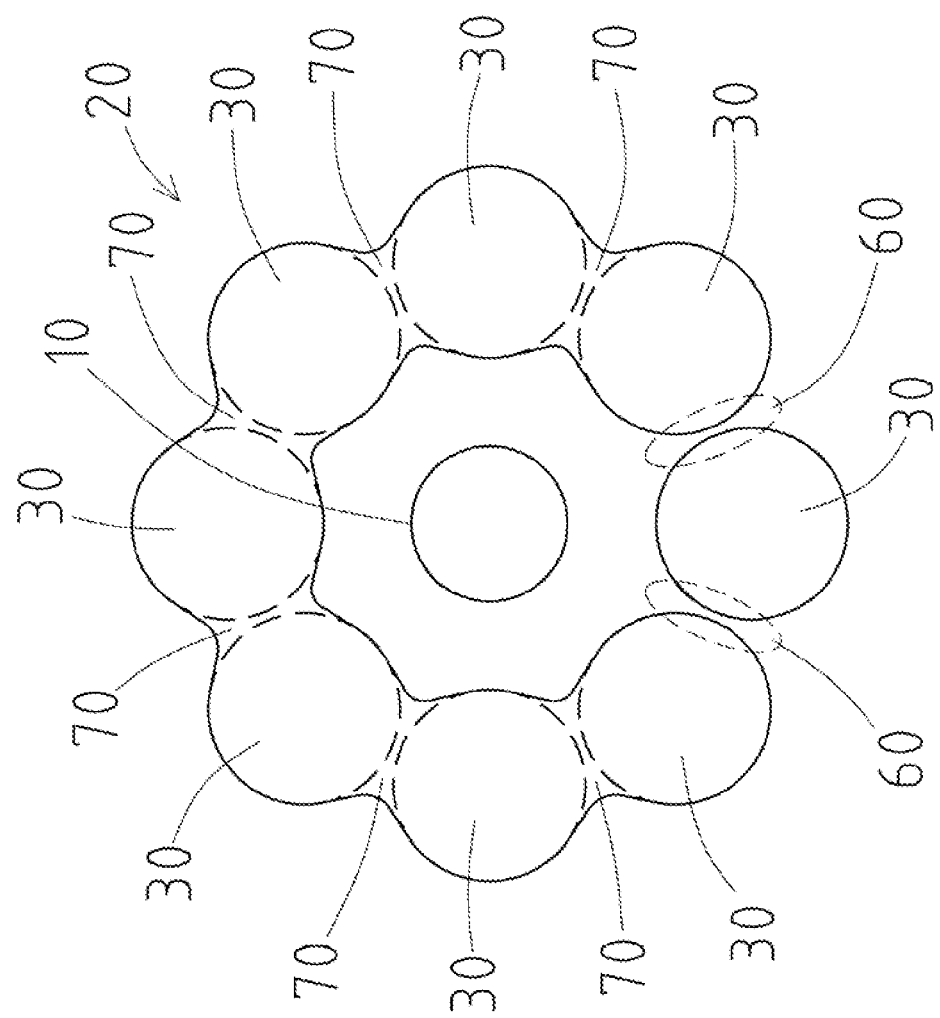
FIG. 2 shows the A-A cross section in FIG. 1.

First, as shown in FIG. 1, the guide wire 1 comprises a core shaft 10, a coil body 20 covering the distal end portion of the core shaft 10 and formed with spirally wound multiple element wires 30, and a distal end fixed portion 40 by which the distal end of the core shaft 10 is fixed to the distal end of the coil body 20. The proximal end of the coil body 20 is fixed to the core shaft 10 by the proximal end fixed portion 50.

As shown in FIG. 2, the coil body 20 is formed with 8 element wires 30. The coil body 20 can be formed, for example, by densely twisting the 8 element wires 30 on a core bar so that they make contact with each other, and thereafter removing residual stress by a known heat treating method, and then pulling out the core bar. Note that the number of the element wires 30 of the coil body 20 is to be two or more, but is not limited to eight.

As viewed in cross section, a fixed portion 70 in which the multiple element wires 30 are fixed to each other and a gap portion 60 in which the multiple element wires 30 are not fixed to each other to leave a gap between two adjacent element wires 30 of the multiple element wires 30 are provided at the distal end of the coil body 20 (see FIG. 2). The fixed portion 70 is formed by melting distal portions of adjacent ones of the multiple element wires 30 by laser or electro-discharge machining, but the method is not limited to these techniques. The fixed portion 70 may be formed by fixing another material to a gap between adjacent ones of the multiple element wires 30.

Figure 3:
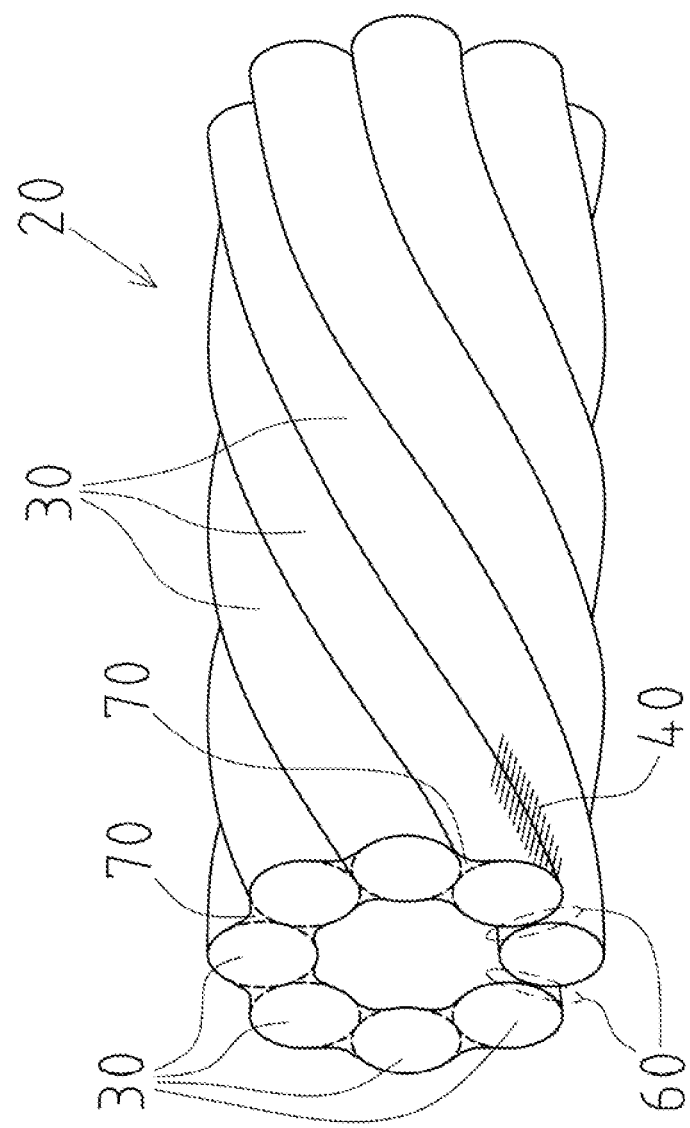
FIG. 3 shows a perspective view of only a coil body of the guide wire shown in FIG. 1.

FIG. 3 shows a perspective view of the coil body 20 alone. The guide wire 1 according to the present embodiment is faulted by fixing the distal end fixed portion 40 to the distal end of the coil body 20 having both the fixed portion 70 and the gap portion 60. Therefore, the distal end fixed portion 40 flows towards the proximal end side along the surfaces of the multiple element wires 30 at the gap portion 60 while the distal end fixed portion 40 does not substantially flow towards the proximal end side at the fixed portion 70 because there is no gap between the multiple element wires 30 at the fixed portion 70. Therefore, as shown in FIG. 3, the distal end fixed portion 40 enters into only the gap portion 60.

As described above, both the fixed portion 70 and the gap portion 60 are provided at the distal end of the coil body 20 in the guide wire 1. Therefore, a risk of unwinding of the multiple element wires 30 of the coil body 20 can be reduced by providing the fixed portion 70. Further, a risk that the distal end fixed portion 40 flows towards the proximal end side along the surfaces of all of the multiple element wires 30 can be reduced even in a case where highly flowable (highly wettable) solder materials and metal solders are used at the distal end fixed portion 40. Further, since the distal end fixed portion 40 enters into the gap portion 60, the tensile strength of the distal end fixed portion 40 can be enhanced, and a risk that the distal end fixed portion 40 becomes detached from the distal end of the coil body 20 can be reduced even when an external force is applied to the distal end of the coil body 20.

Note that as shown in FIG. 2, two gap portions 60 and six fixed portions 70 are provided at the distal end of the coil body 20 in the present embodiment, but the configuration is not limited to this. For example, three gap portions 60 and five fixed portions 70 may be provided at the distal end of the coil body 20. Further, the same number of the gap portions 60 and the fixed portions 70 may be provided at the distal end of the coil body 20, or the number of gap portions 60 provided may be larger than the number of the fixed portions 70.

Next, materials for each member of the guide wire 1 will be described, but they are not limited to these materials in particular.

The core shaft 10 can be formed with a stainless steel (SUS304, SUS316 and the like) and a superelastic alloy such as an Ni—Ti alloy.

The coil body 20 can be formed with multiple element wires 30 which have radiopacity. Examples include gold, platinum, tungsten and alloys comprising these elements. In a case where the coil body 20 is formed with the element wires 30 which have radiopacity, an operator can detect the position of the coil body 20 under radiography imaging.

The distal end fixed portion 40 and the proximal end fixed portion 50 can be formed with a solder material (an aluminum alloy solder, a silver solder, a gold solder and the like) or a metal solder (an Au—Sn alloy, an Ag—Sn alloy and the like).

Figure 4:
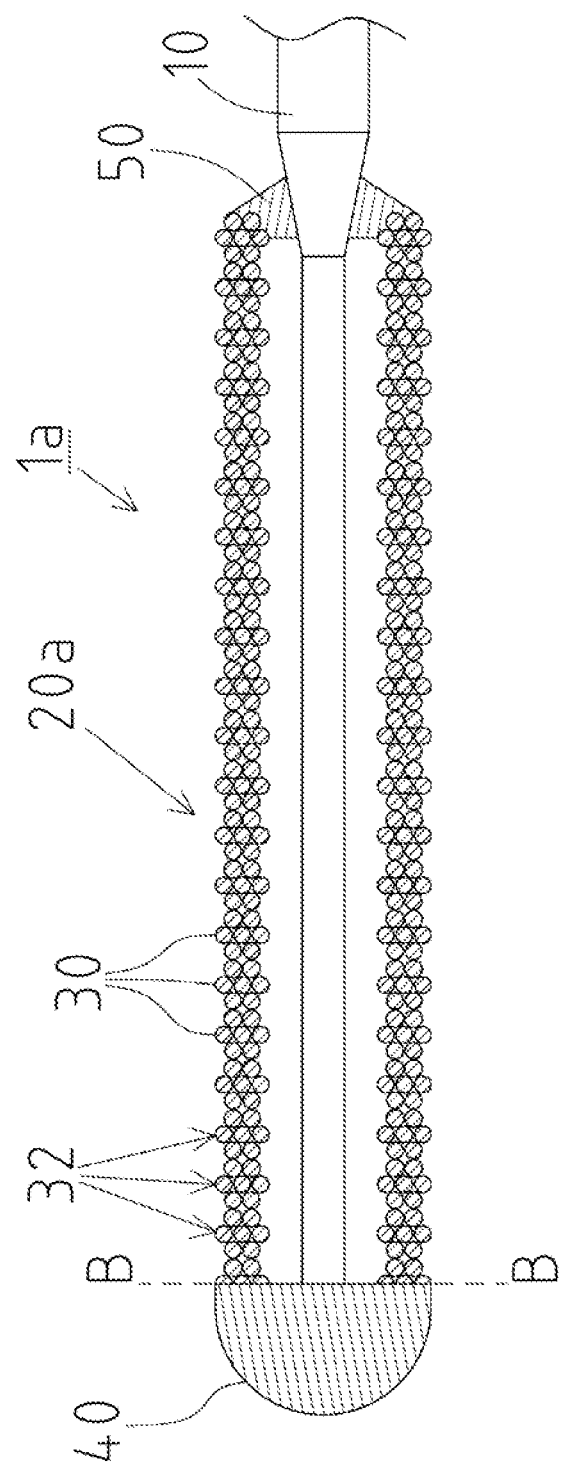
FIG. 4 shows an overall view of a guide wire according to embodiments of the present invention.
Figure 5:
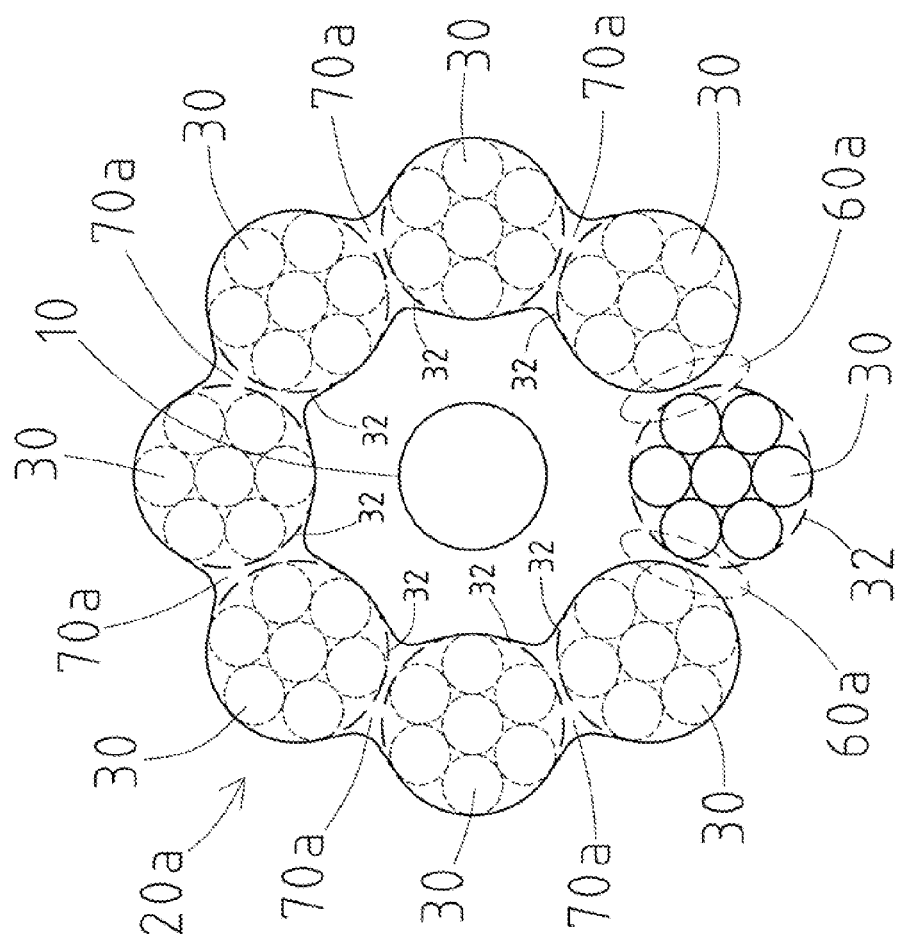
FIG. 5 shows the B-B cross section in FIG. 4.

Next, a guide wire 1a will be described with reference to FIGS. 4 to 7. As in FIGS. 1 and 3, the left side in FIGS. 4 and 6 corresponds to the distal end (the front end) which is to be inserted into the body, and the right side corresponds to the proximal end (the base end) which is to be operated by an operator such as a physician. FIG. 5 shows the B-B cross section in FIG. 4, which is a cross section perpendicular to the longitudinal axis of the guide wire.

Only differences from the guide wire 1 shown in FIGS. 1 to 3 are described below. As shown in FIGS. 4 and 5, in a guide wire 1a, a coil body 20a is formed with spirally wound eight twisted wires 32 in each of which seven element wires 30 are twisted. As viewed in a cross section, a fixed portion 70a in which adjacent ones of the twisted wires 32 having seven twisted element wires 30 are fixed to each other, and a gap portion 60a in which adjacent ones of the twisted wires 32 having seven twisted element wires 30 are not fixed to each other to leave a gap between the twisted wires 32 are provided at the distal end of the coil body 20a.

Note that the number of the twisted wires 32 of the coil body 20a is to be two or more, but is not limited to eight. Similarly, the number of the element wires 30 of the twisted wire 32 is to be two or more, but is not limited to seven.

Figure 6:
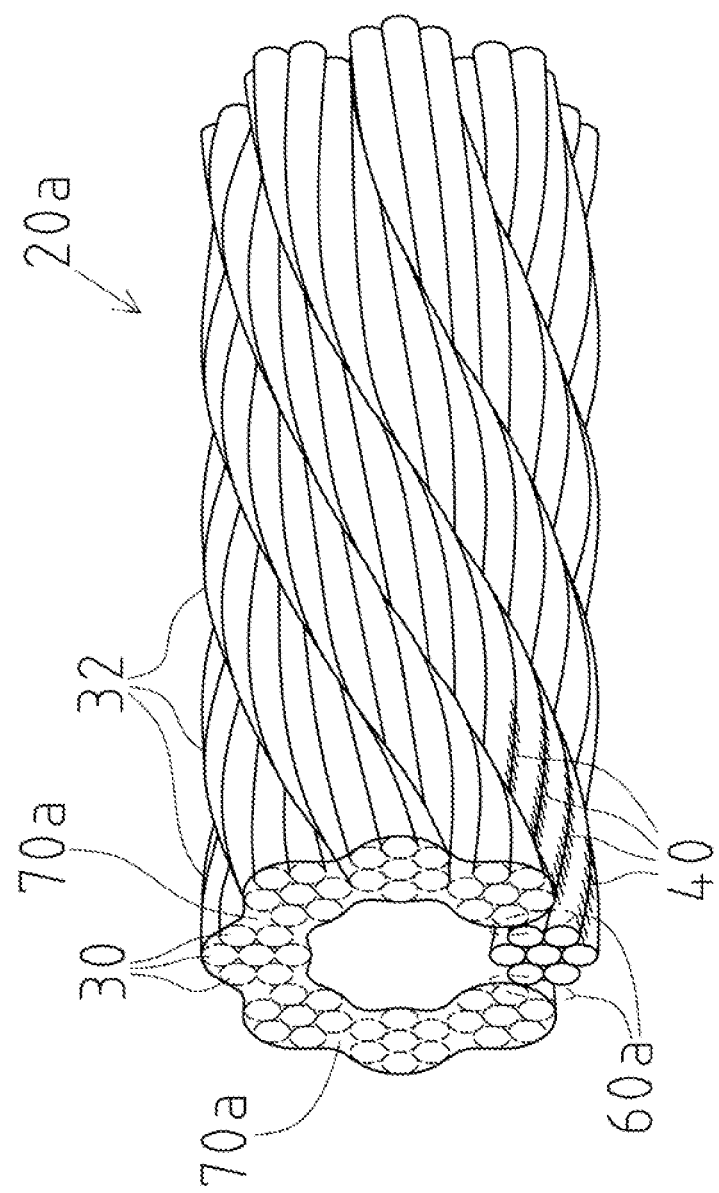
FIG. 6 shows a perspective view of only a coil body of the guide wire shown in FIG. 4.

FIG. 6 shows a perspective view of the coil body 20a alone. The guide wire 1a according to the second embodiment is formed by fixing the distal end fixed portion 40 to the distal end of the coil body 20a having both the fixed portion 70a and the gap portion 60a. Therefore, the distal end fixed portion 40 flows towards the proximal end side at the gap portion 60a along the surfaces of the twisted wires 32 comprising the multiple element wires 30 while the distal end fixed portion 40 does not substantially flow towards the proximal end side at the fixed portion 70a because there is no gap between the multiple twisted wires 32. Therefore, as shown in FIG. 6, the distal end fixed portion 40 enters into the gap portion 60a only.

As described above, in the guide wire 1a, both the fixed portion 70a and the gap portion 60a are provided at the distal end of the coil body 20a as in the guide wire 1. Therefore, a risk of unwinding of the multiple twisted wires 32 of the coil body 20a can be reduced by providing the fixed portion 70a. Further, a risk that the distal end fixed portion 40 flows towards the proximal end side along the surfaces of all of the multiple twisted wires 32 can be reduced even in a case where highly flowable (highly wettable) solder materials and metal solders are used at the distal end fixed portion 40. Moreover, the tensile strength of the distal end fixed portion 40 can be enhanced since the distal end fixed portion 40 enters into the gap portion 60a. Therefore, a risk that the distal end fixed portion 40 becomes detached from the distal end of the coil body 20a can be reduced even when an external force is applied to the distal end of the coil body 20a.

Figure 7:
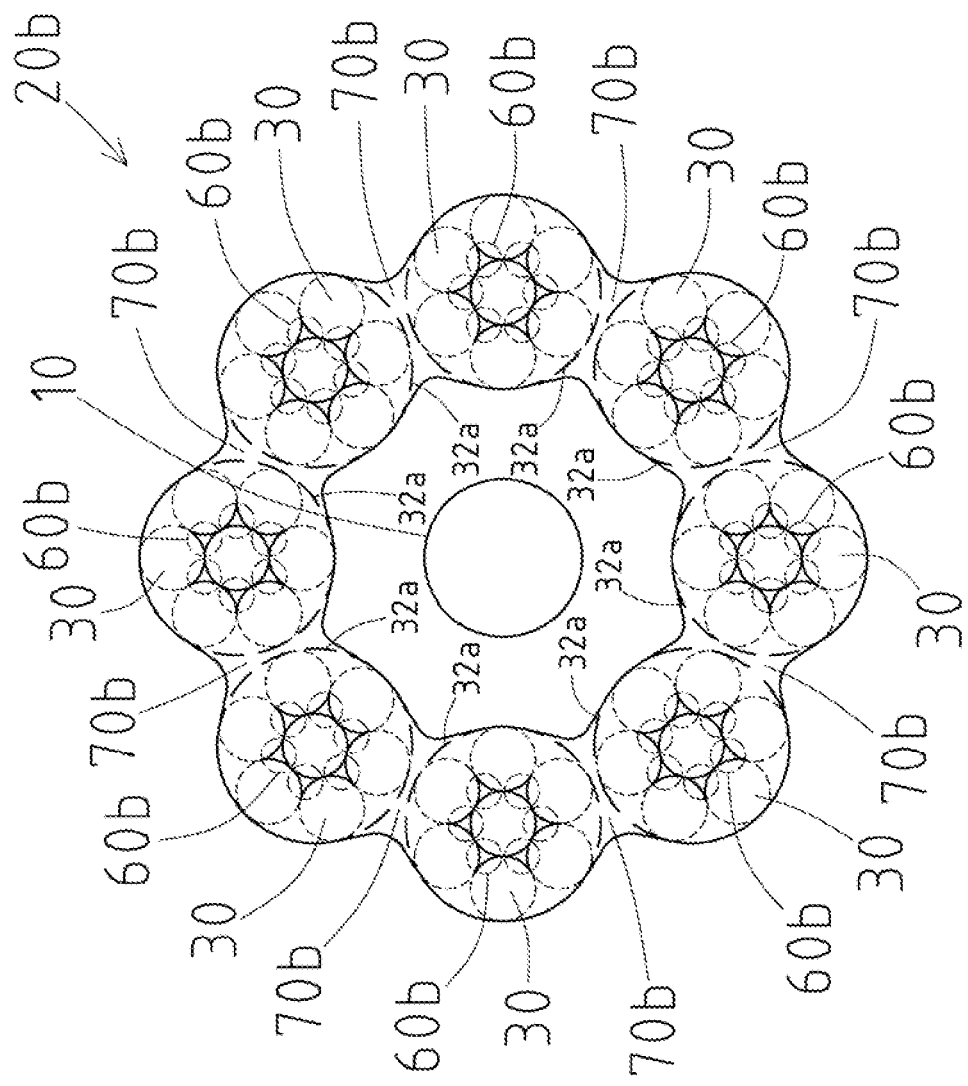
FIG. 7 shows a variation of FIG. 5.

FIG. 7 shows a variation of FIG. 5. In FIG. 5, two gap portions 60a are provided between adjacent twisted wires 32 at the distal end of the coil body 20a. In contrast, in FIG. 7, six gap portions 60b are provided in the inside of one twisted wire 32a at the distal end of the coil body 20b. More specifically described, as shown in FIG. 7, eight fixed portions 70b in which the twisted wires 32a each comprising seven twisted element wires 30 are fixed to each other and six gap portions 60b in the inside of each of the eight twisted wires 32a are provided at the distal end of the coil body 20b as view in a cross section.

The coil body 20b has a degree of freedom and high flexibility because it is formed with the eight twisted wires 32a, but the eight twisted wires 32a of the coil body 20b would unwind more easily as compared with the coil body 20 of the guide wire 1. Nonetheless, as shown in FIG. 7, a risk of unwinding of the distal end of the coil body 20b can be reduced even in a case where the coil body 20b is formed with the twisted wires 32a because the eight twisted wires 32a are all fixed to each other at the eight fixed portions 70b. Further, the distal end fixed portion 40 enters into the gap portions 60b formed in the inside of the twisted wires 32a (in other words, the distal end fixed portion 40 does not flow towards the proximal end side along the surfaces of the twisted wires 32a). Therefore, even in a case where the distal end of the coil body 20b is strongly rubbed with a narrowed or obstructed segment when an operator pushes the guide wire 1a to the narrowed or obstructed segment, a risk can be reduced that the distal end fixed portion 40 which enters into the gap portions 60b peels off from the coil body 20b. As a result, a risk that the distal end fixed portion 40 becomes detached from the distal end of the coil body 20b can be further reduced.

Note that the number of the twisted wires 32a of the coil body 20b is to be two or more, but is not limited to eight. Similarly, the number of the element wires 30 of the twisted wire 32a is to be two or more, but is not limited to seven.

Further, the gap portions 60b are provided in the inside of each of the eight twisted wires 32a in FIG. 7, but the configuration is not limited to this. For example, the gap portions 60b may be provided in the inside of three twisted wires 32b, but not in the inside of the remaining five twisted wires 32c as described below (see FIG. 11). Further, six gap portions 60b are provided in the inside of one twisted wire 32a in FIG. 7, but the configuration is not limited to this. For example, only one gap portion 60b may be provided in the inside of one twisted wire 32a.

Therefore, any configuration may be used as long as the coil body 20b is formed with spirally wound twisted wires 32a comprising twisted multiple element wires 30, and the multiple twisted wires 32a are fixed to each other by the fixed portion 70b, and the gap portion 60b is to be formed somewhere in the inside of at least one twisted wire 32a of the multiple twisted wires 32a.

Figure 8:
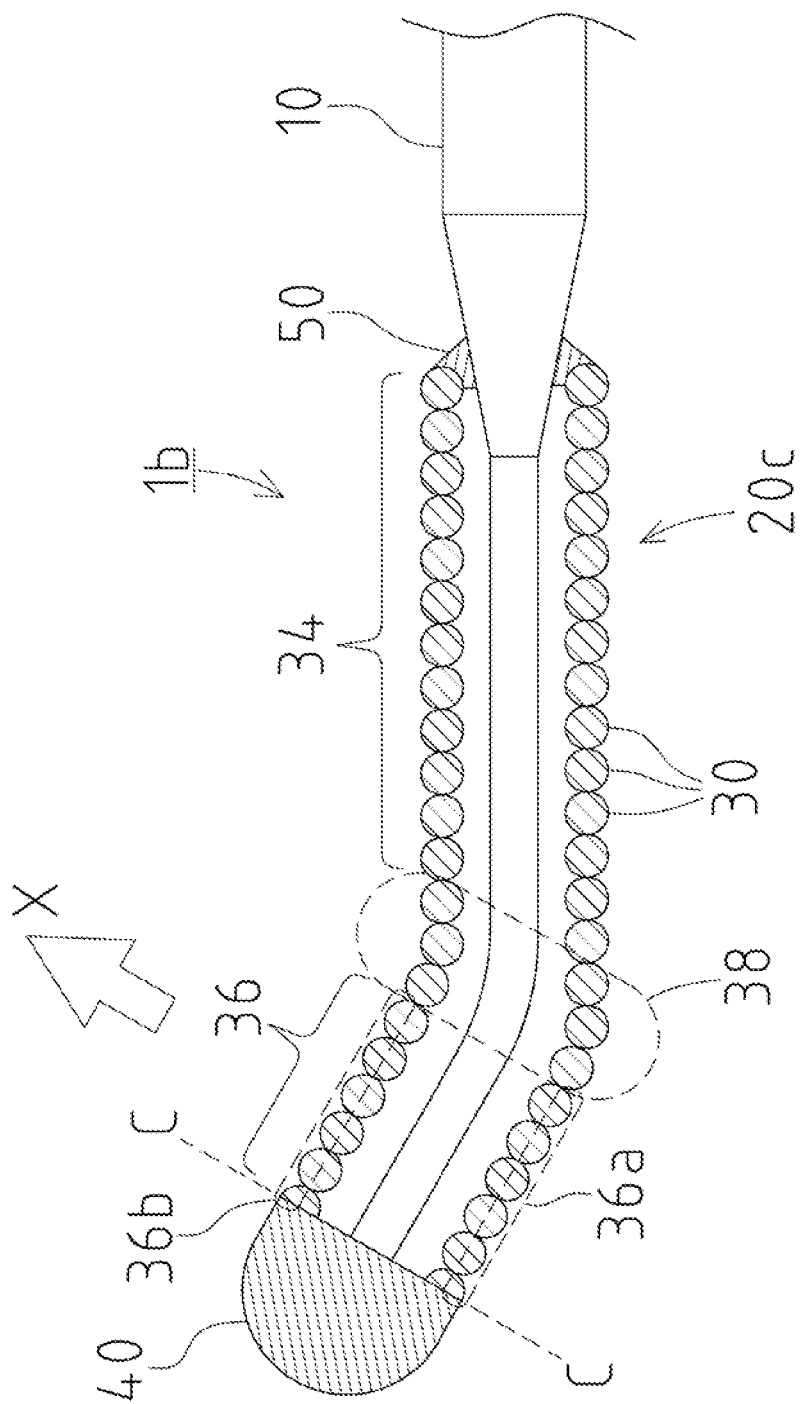
FIG. 8 shows an overall view of a guide wire according to embodiments of the present invention.
Figure 9:
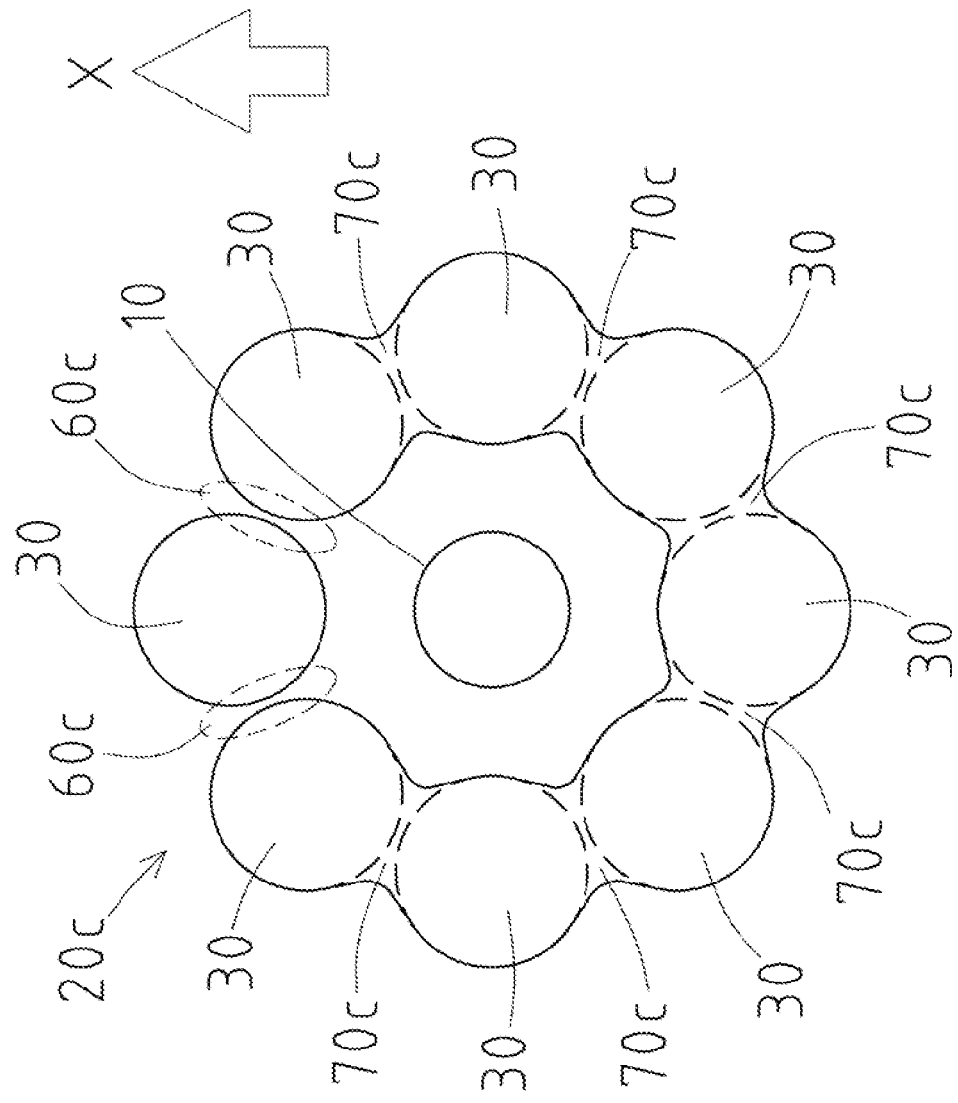
FIG. 9 shows the C-C cross section in FIG. 8.

Next, the guide wire 1b will be described with reference to FIGS. 8 and 9. As in FIG. 1, the left side in FIG. 8 corresponds to the distal end (the front end) which is to be inserted into the body, and the right side corresponds to the proximal end (the base end) which is to be operated by an operator such as a physician. FIG. 9 shows the C-C cross section in FIG. 8, which is a cross section perpendicular to the longitudinal axis of the guide wire.

Only differences from the guide wire 1 shown in FIGS. 1 to 3 will be described below. As shown in FIG. 8, in a guide wire 1b, a coil body 20c comprises a first straight portion 34; a curved portion 38 located distally of the first straight portion 34 and curved in the direction of X; and a second straight portion 36 located between the curved portion 38 and the distal end fixed portion 40.

As shown in FIG. 9, a fixed portion 70c in which the multiple element wires 30 are fixed to each other and a gap portion 60c in which the multiple element wires 30 are not fixed to each other to leave a gap between adjacent ones of the multiple element wires 30 as viewed in a cross section are provided at the distal end of the coil body 20c. At this time, the fixed portion 70c is arranged in the opposite direction of the curvature direction (the direction of X) of the curved portion 38 of the coil body 20c, and the gap portion 60c is arranged in the same direction as the curvature direction (the direction of X) of the curved portion 38 of the coil body 20c.

In the guide wire 1b, the distal end fixed portion 40 easily enters into the gap portion 60c formed in the same direction as the curvature direction (the direction of X) of the curved portion 38 of the coil body 20c. On the other hand, the distal end fixed portion 40 is configured to not easily enter into the fixed portion 70c formed in the opposite direction of the curvature direction (the direction of X) of the curved portion 38 of the coil body 20c. Therefore, the distal end fixed portion 40 does not flow towards the proximal end side along the surfaces of the multiple element wires 30 at an outer periphery side 36a of the second straight portion 36 which likely makes contact with a blood vessel wall or digestive organ wall, while the distal end fixed portion 40 flows towards the proximal end side along the surfaces of the multiple element wires 30 at an inner periphery side 36b of the second straight portion 36 which less likely makes contact with a blood vessel wall or digestive organ wall. As described above, since the distal end fixed portion 40 preferentially enters into the inner periphery side 36b of the second straight portion 36 as compared to the outer periphery side 36a in the guide wire 1b, rigidification due to the distal end fixed portion 40 is less significant at the outer periphery side 36a of the second straight portion 36 of the coil body 20c. As a result, a risk can be reduced that the outer periphery side 36a of the second straight portion 36 of the coil body 20c damages a blood vessel wall or digestive organ wall when the guide wire 1b is inserted into the blood vessel or digestive organ.

Note that, as shown in FIG. 9, two gap portions 60c and six fixed portions 70c are provided at the distal end of the coil body 20c, but the configuration is not limited to this. For example, three gap portions 60c and five fixed portions 70c may be provided at the distal end of the coil body 20c. Further, the same number of the gap portions 60c and of the fixed portions 70c may be provided at the distal end of the coil body 20c.

Next, a guide wire 1c will be described with reference to FIGS. 10 and 11. As in FIG. 4, the left side in FIG. 10 corresponds to the distal end (the front end) which is to be inserted into the body, and the right side corresponds to the proximal end (the base end) which is to be operated by an operator such as a physician. FIG. 11 shows the D-D cross section in FIG. 10, which is a cross section perpendicular to the longitudinal axis of the guide wire.

Only differences from the guide wire 1a shown in FIGS. 4 to 7 will be described below. As shown in FIG. 10, in the guide wire 1c, a coil body 20d comprises a first straight portion 134; a curved portion 138 located distally of the first straight portion 134 and curved in the direction of X; and a second straight portion 136 located between the curved portion 138 and the distal end fixed portion 40.

As shown in FIG. 11, the coil body 20d is formed with spirally wound eight twisted wires 32b, 32c comprising seven twisted element wires 30. As viewed in a cross section, eight fixed portions 70d in which the twisted wires 32b, 32c comprising seven twisted element wires 30 are fixed to each other and six gap portions 60d formed in the inside of each of three twisted wires 32b of the eight twisted wires 32b, 32c are provided at the distal end of the coil body 20d. On the other hand, the gap portions 60d are not provided in the inside of five twisted wires 32c of the eight twisted wires 32b, 32c.

In FIGS. 10 and 11, the twisted wires 32c that do not have the gap portion 60d are arranged in the opposite direction of the curvature direction (the direction of X) of the curved portion 138 of the coil body 20d, and the twisted wires 32b having the gap portion 60d are arranged in the same direction as the curvature direction (the direction of X) of the curved portion 138 of the coil body 20d.

In the guide wire 1c, the distal end fixed portion 40 easily enters into the gap portion 60d formed in the same direction as the curvature direction (the direction of X) of the curved portion 138 of the coil body 20d. On the other hand, the distal end fixed portion 40 is configured to not easily enter into the fixed portion 70d formed in the opposite direction of the curvature direction (the direction of X) of the curved portion 138 of the coil body 20d. Therefore, the distal end fixed portion 40 does not flow into the inside of the multiple twisted wires 32c at an outer periphery side 136a of the second straight portion 136 which likely makes contact with a blood vessel wall or digestive organ wall, while the distal end fixed portion 40 flows into the inside of the twisted wires 32b at an inner periphery side 136b of the second straight portion 136 which less likely makes contact with a blood vessel wall or digestive organ wall. As described above, since the distal end fixed portion 40 preferentially enters into the inner periphery side 136b of the second straight portion 136 over the outer periphery side 136a in the guide wire 1c, rigidification due to the distal end fixed portion 40 is less significant at the outer periphery side 136a of the second straight portion 136 of the coil body 20d. As a result, a risk can be reduced that the outer periphery side 136a of the second straight portion 136 of the coil body 20*d* damages a blood vessel wall and digestive organ wall when the guide wire 1*c* is inserted into a blood vessel or digestive organ.

In the guide wire 1*c*, the gap portions 60*d* are provided in the inside of each of three twisted wires 32*b* of the eight twisted wires 32*b*, 32*c* at the distal end of the coil body 20*d* as shown in FIG. 11, but the configuration is not limited to this. For example, the gap portion 60*d* may be provided in the inside of only one twisted wire 32*b* of the eight twisted wires 32*b*, 32*c*, but not in the inside of the remaining seven twisted wires 32*c*. Further, in FIG. 11, six gap portions 60*d* are provided in the inside of each of the three twisted wires 32*b*, but the configuration is not limited to this. For example, one gap portion 60*d* may be provided in the inside of each of the three twisted wires 32*b*. Therefore, the gap portion 60*d* is to be formed somewhere in the inside of at least one twisted wire 32*b* of the multiple twisted wires 32*b*, 32*c*.

Note that the number of the twisted wires 32*b*, 32*c* of the coil body 20*d* is to be two or more, but is not limited to eight. Similarly, the number of the element wires 30 of the twisted wires 32*b*, 32*c* is to be two or more, but is not limited to seven.

Further, in the guide wires 1, 1*a*, 1*b*, 1*c*, 1*d* described above, the tensile strength of the distal end fixed portion 40 may be improved by grinding the distal end of the coil body 20, 20*a*, 20*b*, 20*c*, 20*d* before fixing the distal end fixed portion 40 to the distal end of the coil body 20, 20*a*, 20*b*, 20*c*, 20*d* to increase the contact area between the fixed portion 70, 70*a*, 70*b*, 70*c*, 70*d* and the distal end fixed portion 40. This can further reduce a risk that the distal end fixed portion 40 becomes detached from the distal end of the coil body 20, 20*a*, 20*b*, 20*c*, 20*d* even in a case where an external force is applied to the distal end of the coil body 20, 20*a*, 20*b*, 20*c*, 20*d*.

As described above, in the guide wires 1, 1*a*, 1*b*, 1*c*, 1*d*, both the fixed portion 70, 70*a*, 70*b*, 70*c*, 70*d* and the gap portion 60, 60*a*, 60*b*, 60*c*, 60*d* are provided at the distal end of the coil body 20, 20*a* 20*b*, 20*c*, 20*d*. This can reduce a risk of unwinding of the multiple element wires 30 or the twisted wires 32, 32*a*, 32*b*, 32*c* of the coil body 20, 20*a*, 20*b*, 20*c*, 20*d*. Further, a risk that the distal end fixed portion 40 flows towards the proximal end side along the surfaces or insides of the multiple element wires 30 or the multiple twisted wires 32, 32*a*, 32*b*, 32*c* can be reduced even in a case where highly flowable (highly wettable) solder materials and metal solders are used at the distal end fixed portion 40. Further, the tensile strength of the distal end fixed portion 40 can be enhanced since the distal end fixed portion 40 enters into the gap portion 60, 60*a*, 60*b*, 60*c*, 60*d*. Therefore, a risk that the distal end fixed portion 40 becomes detached from the distal end of the coil body 20, 20*a*, 20*b*, 20*c*, 20*d* can be reduced even in a case where an external force is applied to the distal end of the coil body 20, 20*a*, 20*b*, 20*c*, 20*d*.

What is claimed is:

1. A guide wire comprising:
   a core shaft;
   a coil body covering a distal end portion of the core shaft and having spirally wound multiple element wires; and
   a distal end fixed portion by which a distal end of the core shaft is fixed to a distal end of the coil body, wherein
   the distal end of the coil body includes (i) a fixed portion in which adjacent ones of the multiple element wires are fixed to each other and (ii) a gap portion in which adjacent ones of the multiple element wires are not fixed to each other to provide a gap between the adjacent ones of the multiple element wires in the gap portion, as viewed in a cross section perpendicular to a longitudinal axis of the guide wire, and
   the distal end fixed portion attaches only at the gap portion of the distal end of the coil body.

2. The guide wire according to claim 1, wherein
   each of the element wires is a twisted wire such that the coil body has spirally wound multiple twisted wires,
   adjacent ones of the multiple twisted wires are fixed to each other by the fixed portion, and
   the gap portion is formed in the inside of at least one twisted wire of the multiple twisted wires at the distal end of the coil body, as viewed in the cross section perpendicular to the longitudinal axis of the guide wire.

3. The guide wire according to claim 1, wherein
   the distal end portion of the coil body is curved in a curvature direction so as to have an inner periphery side and an opposite, outer periphery side relative to the curvature direction,
   the fixed portion is located on the outer periphery side of the coil body, and
   the gap portion is located on the inner periphery side of the coil body.

4. The guide wire according to claim 2, wherein
   the distal end portion of the coil body is curved in a curvature direction so as to have an inner periphery side and an opposite, outer periphery side relative to the curvature direction,
   the fixed portion is located on the outer periphery side of the coil body, and
   the gap portion is located on the inner periphery side of the coil body.

5. The guide wire according to claim 1, wherein
   each of the element wires is a twisted wire such that the coil body has spirally wound multiple twisted wires.

* * * * *